(12) United States Patent
Mosler et al.

(10) Patent No.: US 11,534,317 B2
(45) Date of Patent: Dec. 27, 2022

(54) ORTHOPEDIC JOINT DEVICE AND METHOD FOR CONTROLLING SAME

(71) Applicant: OTTOBOCK SE & CO. KGAA, Duderstadt (DE)

(72) Inventors: Luder Mosler, Duderstadt (DE);
Martin Pusch, Duderstadt (DE);
Alexander Pappe, Gottingen (DE);
Christian Will, Gottingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 14/902,537

(22) PCT Filed: Jul. 2, 2014

(86) PCT No.: PCT/EP2014/001807
§ 371 (c)(1),
(2) Date: Dec. 31, 2015

(87) PCT Pub. No.: WO2015/000588
PCT Pub. Date: Jan. 8, 2015

(65) Prior Publication Data
US 2016/0374834 A1    Dec. 29, 2016

(30) Foreign Application Priority Data
Jul. 3, 2013 (DE) .................. 102013011080.7

(51) Int. Cl.
*A61F 2/70* (2006.01)
*A61F 5/01* (2006.01)
(Continued)

(52) U.S. Cl.
CPC ................ *A61F 2/604* (2013.01); *A61F 2/64* (2013.01); *A61F 2/70* (2013.01); *A61F 5/0125* (2013.01);
(Continued)

(58) Field of Classification Search
None
See application file for complete search history.

(56) References Cited

U.S. PATENT DOCUMENTS

| 5,181,931 A | 1/1993 | van de Veen |
| 5,545,232 A | 8/1996 | Van de Veen |

(Continued)

FOREIGN PATENT DOCUMENTS

| CN | 1054364 A | 6/1991 |
| CN | 1111122 A | 11/1995 |

(Continued)

OTHER PUBLICATIONS

Computer generated English language translation of SU 1821177 A1, published on Jun. 15, 1993.*

(Continued)

*Primary Examiner* — David H Willse
(74) *Attorney, Agent, or Firm* — Holland & Hart LLP

(57) ABSTRACT

Systems and methods for controlling an orthopedic joint device of a lower extremity, the orthopedic joint device comprising an upper part, a lower part mounted in articulated fashion to the upper part, and a conversion device arranged between the upper and lower parts. The conversion device provides for, during pivoting of the upper part relative to the lower part, mechanical work from a relative movement between the upper and lower parts to be converted and stored in at least one energy store and supplied back to the joint device with a time offset in order to assist the relative movement. The stored energy is converted back and the supply of mechanical work takes place in a controlled manner during the assistance of the relative movement.

21 Claims, 7 Drawing Sheets

(51) Int. Cl.
*A61F 2/64* (2006.01)
*A61F 2/62* (2006.01)
*A61F 2/60* (2006.01)
A61F 2/50 (2006.01)
A61F 2/74 (2006.01)

(52) U.S. Cl.
CPC ........... *A61F 2/74* (2021.08); *A61F 2002/503* (2013.01); *A61F 2002/5006* (2013.01); *A61F 2002/5072* (2013.01); *A61F 2002/5073* (2013.01); *A61F 2002/5075* (2013.01); *A61F 2002/701* (2013.01); *A61F 2002/708* (2013.01); *A61F 2005/0155* (2013.01); *A61F 2005/0167* (2013.01); *A61F 2005/0169* (2013.01); *A61F 2005/0179* (2013.01)

(56) References Cited

U.S. PATENT DOCUMENTS

| | | | |
|---|---|---|---|
| 2003/0120183 A1* | 6/2003 | Simmons | A61F 4/00 600/595 |
| 2006/0249315 A1* | 11/2006 | Herr | A61F 2/60 180/8.1 |
| 2007/0162152 A1* | 7/2007 | Herr | A61F 2/60 623/24 |
| 2010/0312363 A1 | 12/2010 | Herr et al. | |
| 2011/0264230 A1 | 10/2011 | Herr et al. | |
| 2013/0013085 A1 | 1/2013 | Smith et al. | |
| 2015/0202057 A1* | 7/2015 | Zahedi | A61F 2/64 623/26 |

FOREIGN PATENT DOCUMENTS

| | | | | |
|---|---|---|---|---|
| CN | 2420985 A | | 2/2001 | |
| CN | 2542221 Y | | 4/2003 | |
| CN | 2382384 Y | | 5/2006 | |
| CN | 101518472 A | * | 9/2009 | ............... A61F 2/62 |
| DE | 102008045113 A1 | | 3/2010 | |
| EP | 1532951 A1 | | 5/2005 | |
| RU | 1821177 A1 | * | 6/1993 | ............... A61F 2/60 |
| WO | 2007025116 A2 | | 3/2007 | |
| WO | 2010/064063 A1 | | 6/2010 | |

OTHER PUBLICATIONS

U.S. Appl. No. 61/675,347, filed Jul. 25, 2012.*
PCT International Search Report for PCT International Patent Application No. PCT/EP2014/001807, dated Sep. 23, 2014.

* cited by examiner

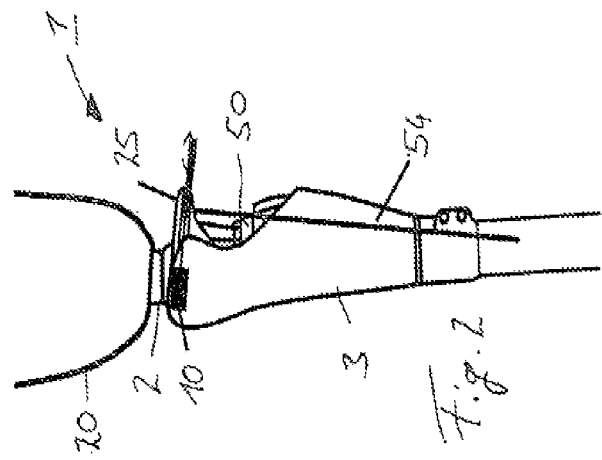
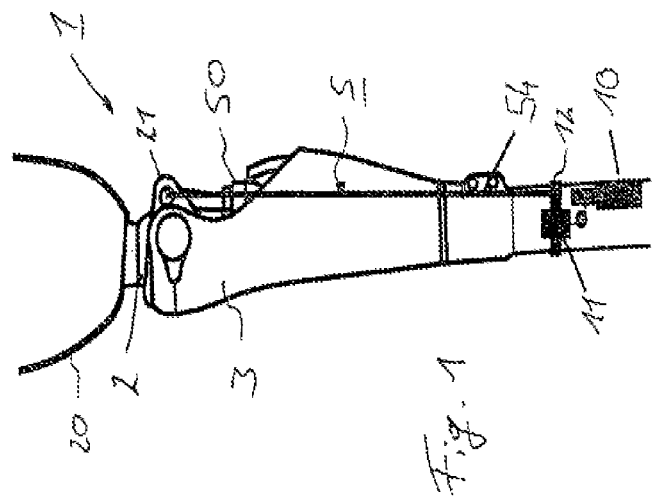

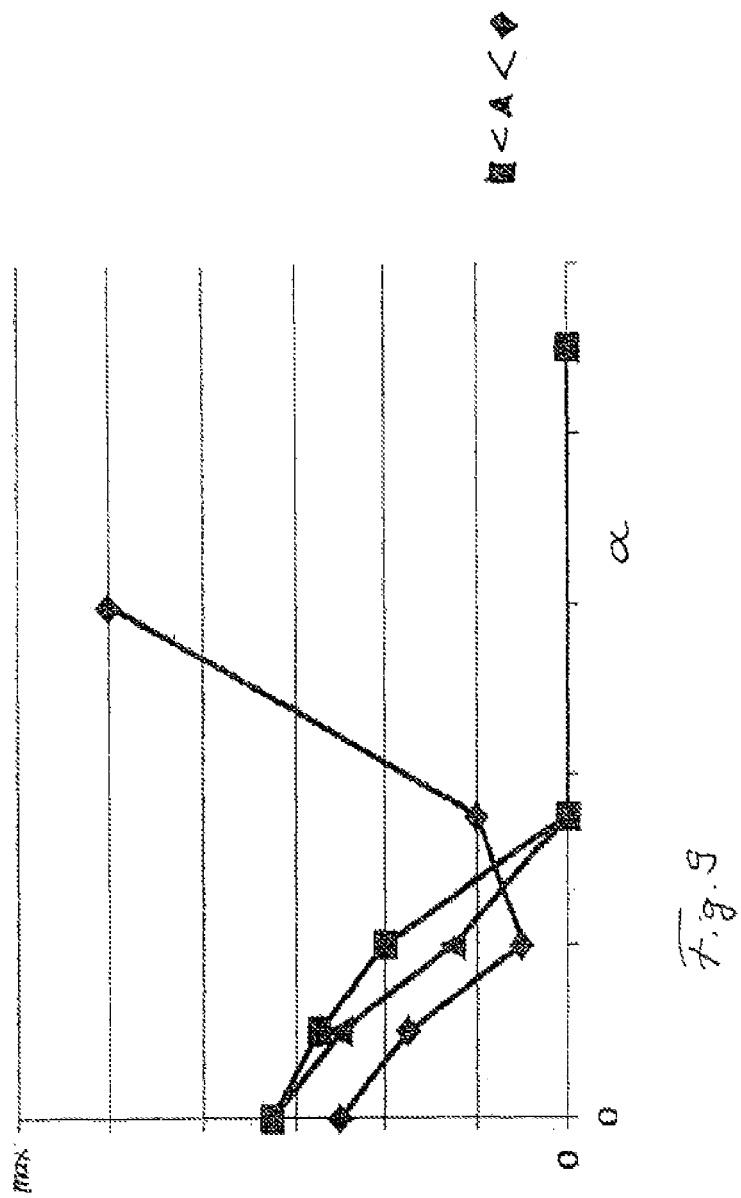

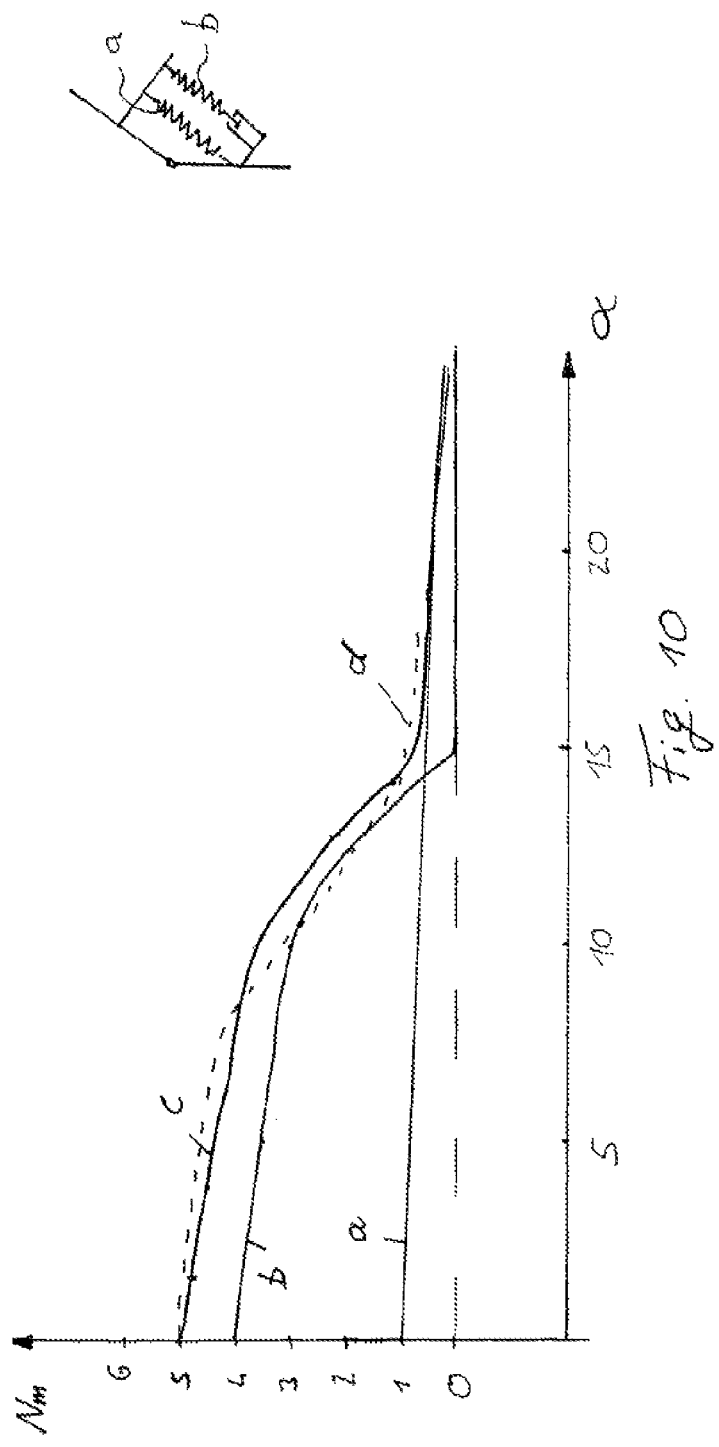

ORTHOPEDIC JOINT DEVICE AND METHOD FOR CONTROLLING SAME

TECHNICAL FIELD

The invention relates to a method for controlling an orthopedic joint device of a lower extremity with an upper part and a lower part mounted thereon in an articulated manner, between which a conversion device is arranged, by means of which mechanical work from the relative movement during a pivoting of the upper part relative to the lower part is converted and stored in at least one energy store and re-supplied to the joint device in a time-offset manner in order to assist the relative movement. The invention likewise relates to an orthopedic joint device of a lower extremity with an upper part and a lower part mounted thereon in an articulated manner, between which a conversion device is arranged, by means of which mechanical work from the relative movement during a pivoting of the upper part relative to the lower part is converted and stored in at least one energy store and re-supplied to the joint device in a time-offset manner in order to assist the relative movement. Such an orthopedic joint device is advantageous, in particular, for prostheses, but it can also be used in orthoses.

BACKGROUND

Most prostheses of the lower extremity are constructed in such a way that movement energy is only converted into heat in order to influence the behavior of the prosthesis; there predominantly is no active supply of energy. By way of example, the prosthesis user controls a prosthetic knee joint when walking by way of his stump with the hip muscles. In this case, experiments from the gait laboratory have shown that this type of walking requires more energy than the walking of healthy subjects. Prosthesis users must apply substantially greater amounts of energy than healthy subjects, particularly in the case of slow walking and alternating climbing of steps.

If energy is supplied to the prosthesis or orthosis during specific phases of walking, the prosthesis or orthosis user needs to apply less of his own energy, the good ground clearance during the swinging phase can be increased and, overall, the movement becomes more comfortable and pleasant.

There are so-called active prosthetic knee joints, in which a drive emulates the whole movement pattern; in this case, the motor is designed in such a way that the conventional gaits can be mapped. As a consequence, the motor must be designed to be relatively powerful and the supply of energy is correspondingly difficult. In the case of sufficiently powerful motors, a malfunction in the controller may constitute a risk to the user. If the motor is designed to be less powerful, it is no longer possible to cover the whole gait spectrum. A further disadvantage consists in the user being forced to follow the movement after a specific movement has been introduced, even if the situation or the intent of the user has changed. Then, the user can no longer influence the movement and he is moved.

In addition to prosthetic knee joints driven purely by a motor, US 2010/0312363 A1 has disclosed a prosthetic knee joint with motors and spring stores, in which energy from the movement is stored in the springs for reducing the drive outlay and released again after reaching a specific angular position. Here, the assistance can be dimensioned in such a way that walking in the plane, or the climbing of steps, is made possible.

SUMMARY

It is an object of the present invention to provide a method for controlling an orthopedic joint device and such a joint device, by means of which it is possible to use an orthopedic joint device intuitively, provide high levels of safety and enable a long usage duration.

According to the invention, this object is achieved by a method having the features of the main claim or by a device with the features of the coordinate claim. Advantageous embodiments and developments of the invention are disclosed in the dependent claims, the description and the figures.

The method according to the invention for controlling an orthopedic joint device of a lower extremity with an upper part and a lower part mounted thereon in an articulated manner, between which a conversion device is arranged, by means of which mechanical work from the relative movement during a pivoting of the upper part relative to the lower part is converted and stored in at least one energy store and re-supplied to the joint device in a time-offset manner in order to assist the relative movement, provides for the stored energy to be reconverted and for the supply of mechanical work for and during assisting the relative movement to be carried out in a controlled manner. When energy is released from an energy store, for example a spring, the stored energy is abruptly supplied to the joint device, i.e. the system of upper part and lower part and an articulated mount, in the prior art in such a way that a large amount of energy is introduced over a very short period of time. According to the invention, provision is made for the stored energy to be re-supplied to the system in a controlled manner and to be converted into mechanical work and assistance for the displacement of upper part in relation to lower part in order to assist the movement over a relatively long period of time such that a movement of the prosthetic or orthotic device which approximates the natural motion sequence can be carried out. An adaptation to modified gaits, the speeds or different patients can only be carried out with extraordinary amounts of outlay in accordance with the prior art by virtue of use being made of specially adapted springs, which is impractical for daily use. By contrast, the energy release into the system is controlled in such a way according to the invention that the required amount of energy can be fed in over a comparatively long period of time in order to influence the gait as desired.

The supply of mechanical work can be modified by virtue of energy being externally supplied to, or removed from, the energy store. If the energy store is a spring, the energy can be supplied by virtue of the spring being re-tensioned; the removal or reduction in the amount of energy can be brought about by the spring being relaxed, for example by displacing a spring abutment. If the energy store is embodied as an electrical energy store, for example as a capacitor, battery or accumulator, the change in the amount of energy can be brought about by activating a generator or by way of an introduction from a second energy store; the reduction in the amount of energy can be brought about by connecting a load or by means of a diversion into a second store for electrical energy.

A development of the invention provides for an actuator to be assigned to the energy store, by means of which actuator the energy store is filled to a minimum level if the relative movement is insufficient therefor. If the energy available as a result of the movement should not be sufficient to supply the energy store with a sufficient amount of energy for the next step or the movement pattern, wherein the minimum amount is dependent on the walking speed, the walking situation and the individual situation of the patient, provision is made according to the invention for the energy store to be filled to a set level during the walking and before the return of energy to assist the relative movement, for example by tensioning a spring or driving a generator which charges the electrical energy store.

In order to be able to precisely determine the time of the movement assistance, provision is made according to the invention for a release device to be assigned to the energy store, by means of which release device the energy is partly or wholly released from the energy store. The release device determines the time of energy release, the duration and the profile of the energy release is not controlled by the release device in the case of complete release; this is controlled by changes in the energy store, i.e. by the removal or supply of energy. In the case of a partial release, there was a reduction in the amount of energy released such that the initial level of the movement assistance can be set. By way of a partial release, an adaptation can be carried out to, for example, walking speeds, patients or walking situations; the fine influencing of the assistance is carried out by way of the change in the energy store.

The mechanical work can be supplied in a manner dependent on a criterion or a combination of a plurality of criteria, namely on the angular position of the upper part relative to the lower part, the position of the upper part and/or the lower part in space, an angular velocity of the upper part and/or the lower part and/or the relative velocity between upper part and lower part and/or the load situation and/or the acceleration of the upper part and/or the lower part, such that there is an assistance of the movement which is as exact as possible in terms of time and amount. The positions of the upper parts and lower parts relative to one another and in space can be determined by angle sensors or inertial sensors, the velocities in relation to one another or within space, or the accelerations, can be established by acceleration sensors or a combination of angle sensor and acceleration sensor, and the load situations can be established by way of force sensors. By way of the sensors, it is possible to determine not only the time of the release of the energy but also the respective gait situation, the walking speed and the current position of the respective components in relation to one another or in space, by way of which it becomes possible to determine and control the amount and the profile of the energy supply for the purposes of assisting the movement.

A development of the invention provides for the energy to be removed from, or re-supplied to, the energy store in a manner dependent on a criterion or a combination of a plurality of criteria, namely the angular position of the upper part relative to the lower part, the position of the upper part and/or the lower part in space, an angular velocity of the upper part and/or the lower part and/or the relative velocity between the upper part and the lower part and/or the load situation and/or the acceleration of the upper part and/or the lower part, in order to enable the controlled regulation of the movement.

The time of engagement of the conversion device can be adjusted in order to modify the amount of energy to be converted and/or the amount of energy supplied so that, for example, it is possible to set, in a manner dependent on the walking speed, the walking situation or the individual parameters of the patient, the magnitude that the amount of energy to be stored needs to be or the magnitude that the amount of energy to be emitted needs to be. In the case where a large amount of energy is desired, provision is made for an engagement in the conversion to take place as early as possible such that, for example, a generator is driven very early on and for a long time or a spring is pretensioned very far in order to convert the mechanical work when walking, for example upon heel strike during the standing phase flexion, to the maximum extent into the potential energy of a spring or electrical energy of an accumulator or of a capacitor. If the time of the engagement during the reconversion is adjusted, for example by displacing a stop or by virtue of an angle-dependent release, the energy is introduced at a later time within the step, as a result of which a change of the gait can be achieved. The energy store can be charged by an actuator if the conversion device is not active due to the relative movement between the upper part and the lower part such that the actuator need not work against the relative movement. Moreover, the temporal categorization of the charging of the energy store by the actuator in a phase in which no mechanical work from the joint device is converted is advantageous in that energy can be stored over a relatively long period of time, leading to it being possible to dimension the actuator in a correspondingly small manner in order to be able to provide the desired amount over a long period of time. By way of example, if a spring is tensioned by way of a motor as an actuator, the latter can have a small configuration and it can be coupled to the spring with a transmission mechanism such that the spring can be tensioned over a comparatively long period of time. The same applies to the conversion and storage of electrical energy.

A development of the invention provides for the relative movement to be additionally influenced by way of a damper device in addition to the influence of the energy store such that the control need not take place only by way of the energy store, leading to a large variation possibility being available when influencing the gait. Moreover, load peaks can easily be caught by way of an additional damper device.

The orthopedic joint device of a lower extremity with an upper part and a lower part mounted thereon in an articulated manner, between which a conversion device is arranged, by means of which mechanical work from the relative movement during a pivoting of the upper part relative to the lower part is converted and stored in at least one energy store and re-supplied to the joint device in a time-offset manner in order to assist the relative movement, provides for an actuator to be assigned to the energy store, which actuator supplies energy to, or removes energy from, the energy store in a controlled manner when assisting the relative movement. As a result of the controlled supply of energy to, or the controlled removal of energy from, the energy store by way of an actuator, particularly simple and reliable influencing of the gait is made possible in the case of semi-active joint devices, in particular in the case of semi-active prosthetic knee joints.

The conversion device can be embodied as a spring or transducer, e.g. a generator, in order to store the mechanical work, which accrues in the case of a relative movement between the upper part and the lower part, either as potential energy in a spring or as electrical energy in an electric storage device, for example in the form of an accumulator, in a rechargeable battery or in a capacitor or in another form of energy.

The energy store can be embodied as a spring, spring mechanism, e.g. a pressure store in conjunction with fluid actuators, or as an accumulator, wherein an accumulator is also understood to mean a capacitor or a rechargeable battery.

A separate damper device can be arranged between the upper part and the lower part in order to be able to control the relative movement better in the case of assistance by the energy store. There can be more precise and more reliable influencing of the gait as a result of the superposition of the influence of the energy store and the separate damper device.

The separate damper device has an adjustable embodiment in order to provide adapted damping in a manner dependent on sensor data, for example in respect of the joint angle, the walking velocity, an angular velocity or an absolute angle of a lower part and/or of an upper part. The damper device can be adjusted by way of an actuator in order to achieve a reduction or an increase in the damping.

The conversion device can be coupled in an adjustable manner to the upper part and/or the lower part in order to displace an engagement position or an adjustment travel. As a result, it is possible to influence both the amount of energy and the time of the energy supply as desired.

The conversion device, the energy store or both components can have a combination of at least two springs, which are effective over different angular ranges of the joint device. The springs can have different spring constants such that a force supply that is adapted to the requirements of the respective movement is made possible. By way of example, if provision is made for a swinging-phase initiation of the knee joint to be assisted or introduced by way of the conversion device, what needs to be taken into account is that an assistance moment, i.e. torque, required herefor is nonlinear. A nonlinear assistance moment can be produced by way of a linear spring if the latter is influenced in terms of the behavior thereof by way of a damper and/or an actuator. In order to avoid the outlay necessary for this, it is possible to couple or interconnect two or more springs, wherein the springs may have different spring characteristics or spring constants and they are effective over different angular ranges. By way of example, if a high assistance moment is required at the start of the bending, this can easily be achieved by a spring combination connected in parallel or in series. The angular dependence can be achieved by a longitudinal guidance of one of the springs which, for example, is guided in a slot or in a telescopic manner from complete relaxation onward, and so there is no effect of this spring on the movement. A second spring or further springs, for example with a different spring constant or spring length, acts or act over a longer period of time or over a larger pivoting angle of the joint device. In the case of a parallel connection, a nonlinear profile emerges, to which the desired moment profile can easily be adapted. Advantageously, the use of a damper is not necessary for adapting the moment profile, and so less energy is converted into heat that cannot be used. If only one spring were present, it would have to be designed thicker and the excess energy in certain phases of the bending movement would have to be damped away. Moreover, there is no need for any outlay such as a damper regulation.

BRIEF DESCRIPTION OF THE DRAWINGS

Exemplary embodiments of the invention will be explained in more detail on the basis of the following exemplary embodiments. The same reference signs denote identical components. In detail:

FIG. 1 shows a joint device with an elastic cord as energy store;

FIG. 2 shows a variant of FIG. 1 with a displaceable spring connection;

FIG. 7 shows a representation of different paths of displacement against a joint angle for various walking speeds;

FIG. 9 shows a representation of a flexion damping setting of a damper against a knee angle; and FIG. 10 shows a representation of a moment profile in the case of springs connected in parallel.

DETAILED DESCRIPTION

Figure 3:
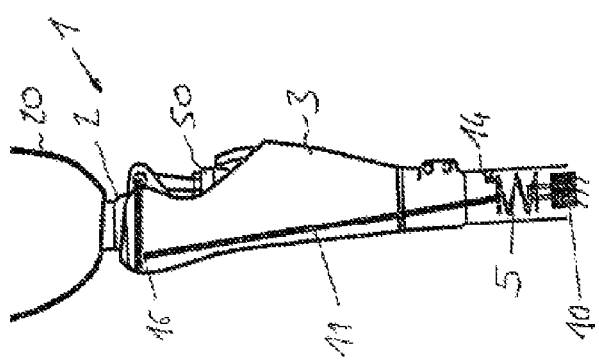
FIG. 3 shows a variant with a spring arranged in the lower part.

FIG. 1 shows an orthopedic joint device in the form of a prosthetic knee joint with an upper part 2, on which an upper leg shaft 20 for receiving an upper leg stump is arranged. A lower part 3 is fastened in an articulated manner distally in relation to the upper part 2, so that the upper part 2 can be pivoted in relation to the lower part 3. Formed on the rear of the upper part 2 is a bracket 21, arranged on which there is on the one hand a damper device 50 in the form of a hydraulic or pneumatic damper and on the other hand an energy store 54 in the form of an elastic cord. The elastic cord is connected by way of a transmission gear mechanism 11 to an actuator 10 in the form of an electric motor. The electric motor is arranged in a lower leg tube, which is fastened to the lower part 3. The energy store 5 in the form of the elastic cord is fastened to the transmission gear mechanism 11 and to a bracket 12; if the motor 10 is activated, it acts by way of the transmission gear mechanism 11 on the bracket 12 and can either tension or relax the elastic cord 54, in that the bracket 12 is displaced in the distal or proximal direction or is turned in one direction or the other, in order to roll up or unroll the elastic cord. The bracket 12 consequently forms a displaceable mounting point of the energy store 5, whereby it is possible in the case of an extension movement of the lower part 3 to set the beginning of a tensioning operation of the elastic cord 54. The bracket 12 can be used to realize a displaceable, elastic stretching limit stop, which is adjusted by way of the actuator 10. The energy store 54, formed as a spring, is tensioned by way of an extension movement of the lower part 10 and takes up part of the kinetic energy of the lower part 3. This may take place for example at the end of the swinging phase or after the heel strike and the standing phase flexion. The spring is tensioned in the course of the standing phase extension and it continues to be kept tensioned during the standing phase.

In the terminal standing phase, the stored energy can be released again to assist the initiation of the swinging phase; the elastic cord 54 is drawn in and it converts the potential energy into mechanical work, in order to assist the flexion of the lower part 3. If more energy is to be stored in the energy store 54, the actuator 10 pretensions the elastic cord 54, in that the bracket 12 is displaced distally or in the rolling-up direction; if less energy is to be stored, the bracket 12 is displaced proximally or the cord is unrolled. In the exemplary embodiment represented, the energy storage device 54 is at the same time the conversion device 5, in which the mechanical work from the relative movement is converted into potential energy.

In addition to the conversion device 5 or the energy store 54, a separate damper 50 is provided in the form of a hydraulic or pneumatic damper, which is of an adjustable design, so that the damper device 50 can be used to influence the damping during walking, both in the direction of flexion and in the direction of extension.

For controlled assistance in the initiation of the swinging phase, it is provided that changing of the pretensioning of the elastic cord 54 takes place by way of the actuator 10, the transmission mechanism 11 and the displacement or turning of the bracket 12, in order to keep a better check on the release of energy. It has been found that a spring alone as the energy store has the effect of introducing too great a force too quickly, which can be perceived by the patients as unpleasant. In order to keep a check not only on the time period over which energy is introduced but also the amount of energy and the power output, a manipulation can be performed on the energy store 54 in dependence on the angular position of the upper part 2 in relation to the lower part 3, the angular position of the upper part 2 and/or the lower part 3 in relation to one another or in space, the angular velocities or the walking speed, in order to limit the power output and additionally control the time sequence of the release of energy. By relaxing the spring 54 it is possible to introduce less energy into the joint device 1; by retensioning the spring 54, it is possible to maintain assistance of the flexion over a longer time period and over a greater flexion angle, in order to achieve the desired harmonious gait pattern.

A variant of the invention is shown in FIG. 2, one in which a displacement at the distal mounting point takes place instead of the relaxing or tensioning of the spring 54 substantially in its longitudinal extent. The upper fastening point is guided in a displaceable spring attachment 25, which by way of the actuator 10 is displaceable back and forth in the direction of the double-headed arrow. Depending on the point of articulation and the direction of movement, the elastic cord 54 is tensioned or relaxed. Both in FIG. 1 and in FIG. 2, the energy from the extension movement is stored in the elastic cord 54. After ending of the extension movement, it is possible that the motor 10 can subsequently retension the cord 54 if the expected energy to be applied is not sufficient to bring about desired assistance in the initiation of flexion. The retensioning advantageously takes place whenever the joint device 1 is in a completely extended state, in order to have to work as little as possible against a pretensioning movement. It is possible by the adjustment either of the pretensioning of the elastic cord 54 or of the proximal mounting position to set the stretching angle from which the conversion device 5 becomes active, whereby how much energy is to be stored in the energy store 5 can also be set.

In FIG. 3, a variant of the joint device 1 is shown, one in which the conversion device 5 in the form of the spring 54 is arranged in the lower leg tube. The actuator 10 is connected to the spring 5 and can either compress it or wind it up, depending on the configuration of the spring as a compression spring or a spiral spring. The spring 5 is coupled by way of a thrust rod 11 to a limit stop 16, which is fastened to the upper part 2. By activation of the motor 10, the bottom point of the spring 5 can be changed, whereby the thrust rod 11 can be used to set when the spring 5 comes into contact with the limit stop 16. The earlier the thrust rod 11 comes into contact with the limit stop 16, the greater the path of adjustment and the compression of the spring 5, so that correspondingly more energy is stored in the spring 5. Accordingly, when it is converted back, more energy is transmitted from the spring by way of the thrust rod 11 to the limit stop 16, so that increased flexion assistance can be achieved. In order to influence the release of energy, the spring 5 is either tensioned or relaxed in the event of movement assistance.

Figure 4:
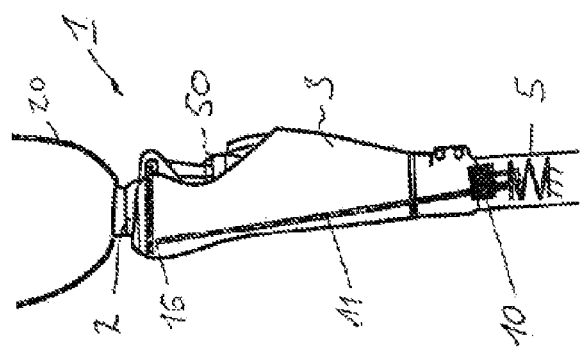
FIG. 4 shows a variant of FIG. 3 with an interposed actuator.

In FIG. 4 there is shown a variant that corresponds substantially to FIG. 3; however, the actuator 10, possibly with a spindle drive and freewheeling in one direction, is arranged between the spring 5 and the thrust rod 11, so that the bottom point of the spring 5 remains fixed, but the spring 5 can be pretensioned with the motor 10. If flexion assistance is initiated, the motor 10 must join in the rotation, in order to release the energy and transmit it by way of the thrust rod 11 and the limit stop 16 to the joint device, whereby particularly good control over the release of energy can be achieved. It is similarly possible to stop the release of energy, which may be advisable if a situation has been misjudged.

Figure 5:
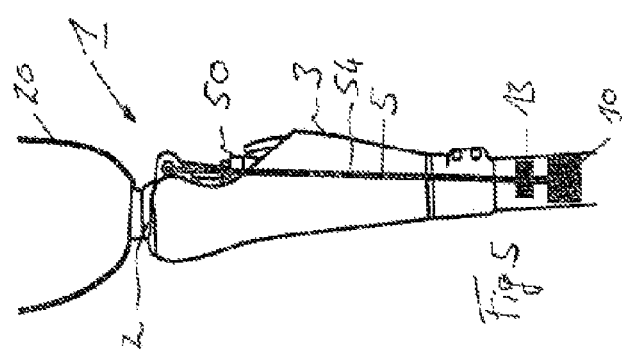
FIG. 5 shows a variant with a twisted filament as an energy store.

In FIG. 5, a twisted filament is shown as the energy store 54 and conversion device 5, in the case of which shortening is achieved by a twisting of filaments. By increasing or decreasing the twisting, the contact point from which the twisted filament builds up tensile forces can be set. Between the motor 10 and the twisted filament 54, an axial decoupling 13 is provided.

Apart from the embodiment shown of the energy store as a spring, by using a transmission gear mechanism and a generator it may possibly also be designed as an electrical energy store in the form of a battery, an accumulator or a capacitor. For converting the stored electrical energy back, the generator is switched as a motor, so that driving and assistance of the relative displacement of the lower part 3 in relation to the upper part 2 can take place. To increase the amount of energy, a generator may be assigned to the electrical energy store; it is similarly possible to provide a further energy store, which serves as a buffer into which excess electrical energy is fed or from which energy that is additionally required is provided.

The springs as energy stores 54 may be designed as tension springs, compression springs, torsion springs or elastomer elements, which from a certain stretching angle, which is set by the actuator 10, come into contact and from this point in time both convert mechanical work into energy and feed it back for movement assistance. The spring in this case takes up the energy from the movement in the direction of extension, and serves at the same time as a decelerating device and extension limit stop. With the initiation of the swinging phase, the energy is released again and it helps the user to initiate the swinging phase. The actuator 10 can be used to adjust the point in time of the contact of the spring in the case of the release of energy, so that different, controlled forms of assistance are possible for different walking speeds. It is similarly possible that the respective spring is retensioned by way of the motor 10, if the energy stored by the preceding movement is not sufficient to provide sufficient assistance; for example, in the case of particularly slow walking or going down steps, the mechanical work may not be sufficient to tension the spring sufficiently. As shown in FIG. 3, the spring 5 may be assigned a releasing device 14, by way of which the initiating time for the release of the stored energy can be additionally ensured.

In order to ensure the triggering of the release, the joint device 1 may include a safety device, which is formed by the hydraulics in the damper 50 or by a control of the motor 10, which ensure that the spring energy applied is reduced again in good time.

On account of the fact that the kinetic energy in the extension is at least partially stored, the assistance provided by the motor can operate very economically. The battery for the actuator 10 can be made small and lightweight, as can the actuator 10 itself, since the actuator 10 has sufficient time when retensioning in the standing phase to tension the spring, and the feeding in of the energy does not have to take place as quickly as the release for the initiation of the swinging phase. The motor 10 controls the release of energy from the spring, possibly in conjunction with the separate damper 20. The flexion assistance provided by the energy store helps in achieving the necessary bending angle in the case of alternating climbing up stairs and when stepping over obstacles, and saves hip work.

Figure 6:
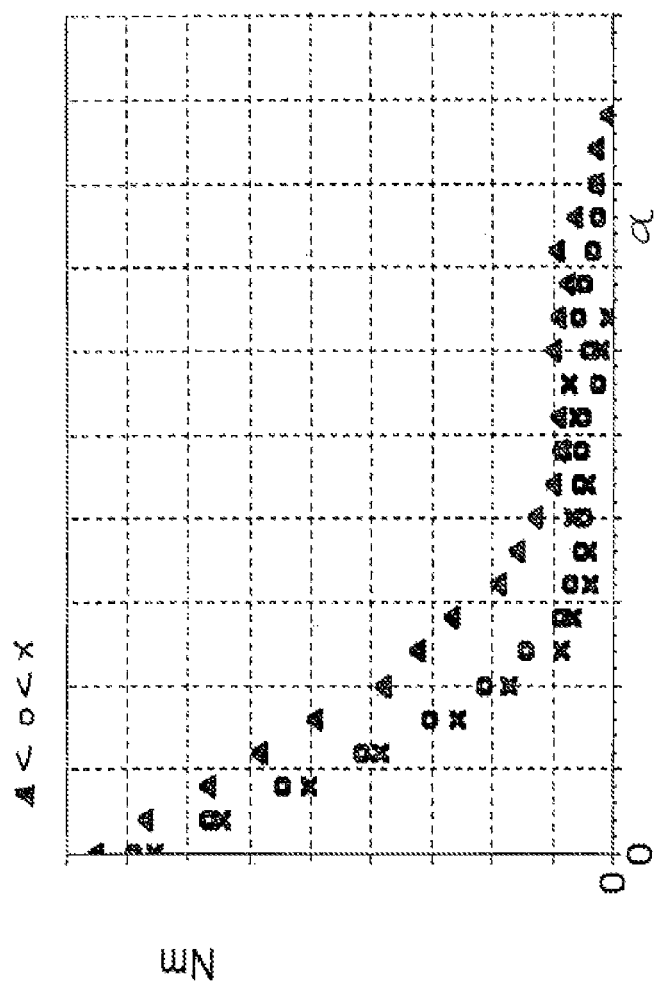
FIG. 6 shows a representation of drive moment profiles for different walking speeds.
Figure 4:
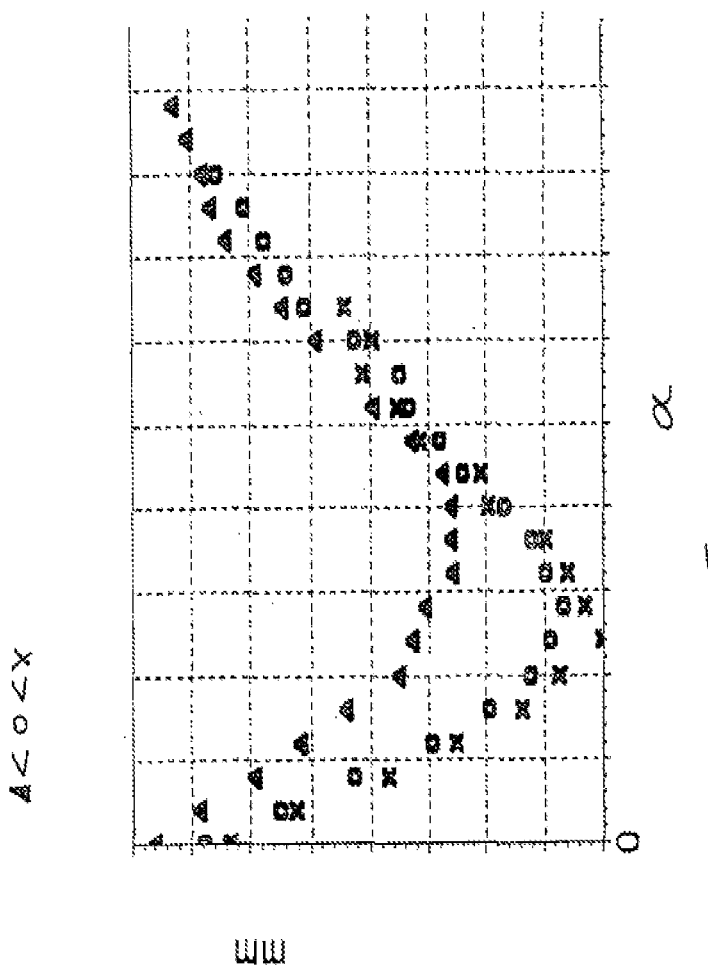

In FIG. 6, the drive moment for different walking speeds is shown against the joint angle $\alpha$. The representation is for three different walking speeds, the respective walking speeds being represented by different symbols in the diagram; the lowest walking speed is identified by a triangle, the medium walking speed by a circle and the highest walking speed by an X. The drive moment is the effective drive moment in Nm, that is to say the energy stored by the storage device 5 and fed back, less the losses such as damping or friction. It is evident that initially a very high drive moment is used in order to be able to provide the flexion assistance at the beginning. With an increasing joint angle $\alpha$, here the knee angle, which is measured from a maximum extension position, the drive moment to be applied initially falls steeply, remains constant over a small angular range, briefly rises again and then, up to maximum flexion, falls to zero. It is evident that the flexion assistance at low walking speeds, represented by the triangle, is greater than at high walking speeds. The drive moment profile, as it is shown in FIG. 6, cannot be produced by retensioning or relaxing a spring without the influence of a motor, since, according to the invention, after a strong drop in the drive moment, the moment is maintained over a further time period up until reaching the maximum angle.

FIG. 7 shows a diagram in which the tension path of the motor 10 is plotted against the joint angle $\alpha$. Various walking speeds are presented, once again identified by a triangle, a circle and an X; the lowest walking speed is represented by a triangle. The representation relates to the translational movement of the motor 10 in the case of the embodiments of FIGS. 1, 3 and 5. The path of displacement according to FIG. 7 is adjusted such that the drive moment curve according to FIG. 6 can be achieved. The respective profile is different for each spring chosen and, depending on the property of the spring, can lead to a greater or smaller path of displacement. The aim is to achieve a displacement, and consequently tensioning, of the spring that is as small as possible. At the start of the initiation of bending, it is evident that the motor allows the spring to slide back, in order to achieve the fastest possible force reduction, in order that the feeling of controlled flexion continues to be maintained. At greater angles, the spring is tensioned again, in order to maintain the force or increase it again. Here, too, it is significant that, at slower walking speeds, increased assistance is necessary. The release of the spring, and consequently of the energy, for flexion assistance and the driving of the motor take place at the same time, so that it is possible to keep a check over the entire profile of the flexion assistance.

Figure 8:
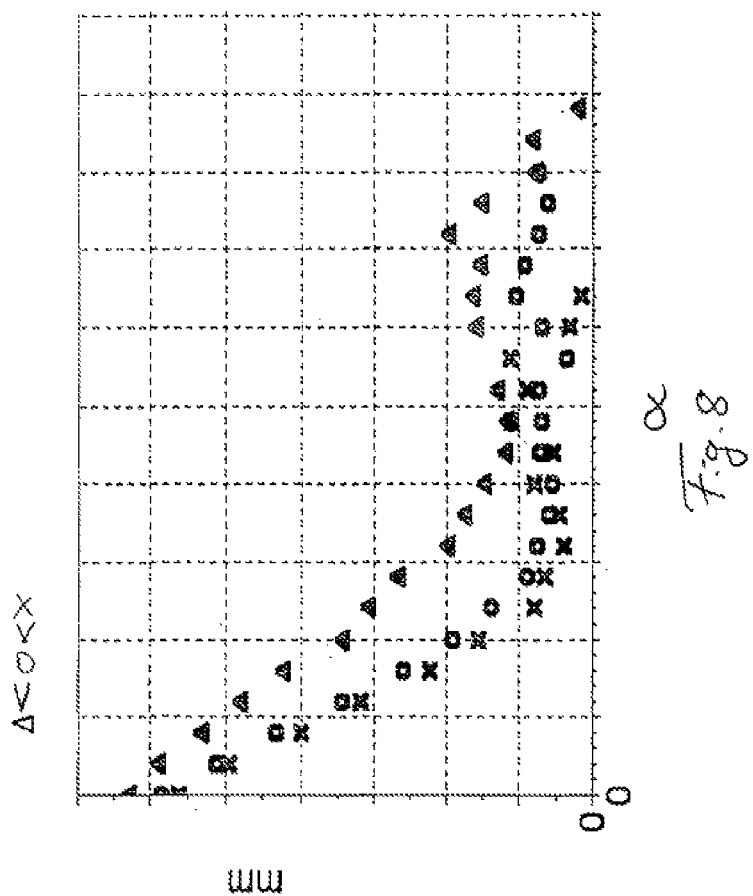
FIG. 8 shows a representation of a lever arm profile against a joint angle.

FIG. 8 shows the change in the lever arm according to an embodiment of FIG. 2 against the joint angle $\alpha$ for different walking speeds. Here, too, at the same time as the release of the spring the motor 10 is activated, in order to adjust the lever arm. Initially, the lever arm is quickly reduced, in order to bring about a reduction in the force; subsequently, the lever arm is increased again, in order to apply force and assist the flexion movement over a greater angular range a.

In FIG. 9, the flexion damping setting of the damper device 50 is shown against the joint angle $\alpha$ for various speeds. As a departure from the previous figures, the lowest walking speed is identified by a square, the medium speed by a triangle and the highest walking speed by a rhomboid. A medium flexion damping setting of the damper device 50 is initially provided, decreasing as the joint angle $\alpha$ increases. At high walking speeds, raising of the flexion damping may take place toward the end of the swinging phase, in order to avoid excessive bending of the lower part 3. By changing the flexion damping setting in the damper unit 50, it is possible in conjunction with the motor control to carry out effective and safe, as well as simple, control of the introduction of energy for movement assistance.

Apart from the embodiment shown as flexion assistance, the device may in principle also be used for extension assistance; the statements made in relation to flexion assistance also apply correspondingly to extension assistance, it also being possible and intended that flexion assistance and extension assistance be arranged together in a joint device.

FIG. 10 depicts a moment profile of two springs a, b connected in parallel, wherein the assistance moment is plotted in Nm against the angle $\alpha$ of the joint angle. The depicted exemplary embodiment relates to a moment profile for an assistance moment during the swinging-phase initiation of an orthotic or prosthetic knee joint. In the swinging-phase initiation, the necessary assistance moment is nonlinear and denoted by a dashed line with the reference sign d. In principle, it is possible to generate such a spring characteristic or such a moment by way of a linear spring, with the latter being coupled to a damper or an actuator in order to influence the linear spring in terms of the behavior thereof. Instead of an actuator or damper, FIG. 10 shows the connecting together of two springs with different spring constants, which springs are active over different angular ranges. The first spring a has a virtually linear moment profile over the various angles $\alpha$. The spring constant is lower than in the case of the second spring b, the latter having a higher spring constant, but only being effective up to an angle of $\alpha=15°$. The combination of the two springs a, b leads to a moment profile c, which is a very good approximation of the desired moment profile d. The moment profile of the spring b provides for it only to be effective up to a bending angle of 15°; thereafter, the stored energy is converted and it no longer contributes to further bending of the knee. By way of example, this can be brought about by virtue of the spring b being embodied as a tension spring and being guided in a longitudinal guide, as depicted in the upper right-hand illustration of a joint with springs a, b connected in parallel. The first spring a is effective over a longer pivoting path or pivoting angle $\alpha$, while the spring b, which is likewise embodied as a tension spring, is embodied and dimensioned in terms of its length in such a way that it no longer contributes to the further bending of the joint after reaching the predetermined angle. The first spring a has a lower stiffness than the second spring b and acts over a longer period of time or angular range, and so the combined moment profile c emerges when the two springs are connected together, which combined moment profile comes very close to the desired moment profile d. The desired profile d can be established from experiments; the moment profile may change for different walking speeds, particularly in the case of a prosthetic knee joint or orthotic knee joint, and so a good compromise for all speeds can be found in the case of an assumed average walking speed.

An advantage of the arrangement is that all the energy stored in the springs a, b can be used for bending the joint and no external energy needs to be applied to an actuator or no energy stored in the springs a, b needs to be dissipated by way of a damper. In the case of only one spring, the latter would need a thicker design and excessive energy in a specific angular range would have to be converted by way of a damper.

The invention claimed is:

1. A method for controlling a semi-active orthopedic joint device of a lower extremity, comprising:
   providing the semi-active orthopedic joint device with an upper part, a lower part mounted to the upper part in an articulated manner, a conversion device arranged between the upper and lower parts and including a spring, an adjustable thrust rod, and a limit stop connected to the upper part and arranged to be contacted by the thrust rod, and a motor operably connected to the spring;
   pivoting the upper part relative to the lower part, mechanically converting with the conversion device mechanical work from the relative movement between the upper and lower parts to energy, and storing the energy in the spring, wherein pivoting the upper part relative to the lower part tensions the spring, moves the adjustable thrust rod, and contacts the limit stop with the adjustable thrust rod;
   re-supplying the energy from the spring to the joint device in a time-offset manner in order to assist relative movement of the upper and lower parts; and
   reconverting the stored mechanical work in a controlled manner to assist relative movement of the upper and lower parts, the motor being operable to supply energy to or remove energy from the spring to control an amount of energy available from the spring to assist relative movement of the upper and lower parts.

2. The method as claimed in claim 1, wherein the supply of mechanical work is modified by energy being externally supplied to, or removed from, the spring.

3. The method as claimed in claim 1, comprising:
   determining that the stored mechanical work is insufficient to assist relative movement of the upper and lower parts; and
   filling the spring using the motor to a minimum level based upon the stored mechanical work being insufficient to assist relative movement of the upper and lower parts.

4. The method as claimed in claim 1, wherein a release device is assigned to the spring, the release device being operable to release energy from the spring.

5. The method as claimed in claim 1, wherein the mechanical work is supplied in a manner dependent on at least one of:
   an angular position of the upper part relative to the lower part;
   a position of at least one of the upper part and the lower part in space;
   an angular velocity of at least one of the upper part and the lower part;
   a relative velocity between the upper part and the lower part;
   a load situation;
   an acceleration of at least one of the upper part and the lower part.

6. The method as claimed in claim 1, wherein the spring is configured to store energy, and the energy is supplied or removed in a manner dependent on at least one of:
   an angular position of the upper part relative to the lower part;
   a position of at least one of the upper part and the lower part in space;
   an angular velocity of at least one of the upper part and the lower part;
   a relative velocity between the upper part and the lower part;
   a load situation;
   an acceleration of at least one of the upper part and the lower part.

7. The method as claimed in claim 1, comprising:
   determining that the conversion device is not active due to the relative movement between the upper part and the lower part and;
   charging the spring using the motor based upon the conversion device not being active due to the relative movement between the upper part and the lower part.

8. The method as claimed in claim 1, wherein the relative movement is influenced by a damper device.

9. The method as claimed in claim 1, wherein re-supplying the energy from the at least one spring to the joint device occurs after initiation of the relative movement.

10. The method as claimed in claim 1, wherein the motor is operable to adjust when the rod contacts the limit stop during relative movement between the upper and lower parts, thereby controlling an amount of energy stored in the spring.

11. A semi-active orthopedic joint device of a lower extremity, comprising:
    an upper part;
    a lower part mounted to the upper part in an articulated manner;
    a conversion device arranged between the upper and lower parts, the conversion device including a spring, an adjustable thrust rod, and a limit stop, the limit stop connected to the upper part and arranged to be contacted by the thrust rod, the conversion device being operable to mechanically convert mechanical work from relative movement between the upper and lower parts to energy stored in the spring, the conversion device being operable to re-supply the energy to the joint device in a time-offset manner in order to assist the relative movement; and
    a motor operably connected to spring, the motor being operable to supply energy to or remove energy from the spring to control an amount of energy available from the spring to assist relative movement of the upper and lower parts, wherein pivoting the upper part relative to the lower part tensions the spring, moves the adjustable thrust rod, and contacts the limit stop with the adjustable thrust rod.

12. The semi-active orthopedic joint device as claimed in claim 11, further comprising a separate damper device arranged between the upper part and the lower part.

13. The semi-active orthopedic joint device as claimed in claim 12, wherein the separate damper device is adjustable.

14. The semi-active orthopedic joint device as claimed in claim 11, wherein the conversion device is adjustably coupled to at least one of the upper part and the lower part in order to displace an engagement position or an adjustment travel.

15. The semi-active orthopedic joint device as claimed in claim 11, wherein at least one of the conversion device and the spring has a combination of at least two springs, the at least two springs being effective over different angular ranges of the joint device.

16. The semi-active orthopedic joint device as claimed in claim 15, wherein the at least two springs have different spring constants.

17. The semi-active orthopedic joint device as claimed in claim 11, wherein the conversion device re-supplies the mechanical work to the joint device after initiation of the relative movement.

18. A semi-active orthopedic joint system of a lower extremity comprising:
an upper part;
a lower part movable relative to the upper part about a rotation joint;
a conversion device arranged between the upper part and the lower part and across the rotation joint, the conversion device including at least one spring, an adjustable thrust rod, and a limit stop, the limit stop connected to the upper part and arranged to be contacted by the thrust rod, the conversion device being operable to mechanically convert mechanical work from a first relative movement between the upper and lower parts to energy stored in the at least one spring, and re-supply the energy from the at least one spring to the joint system in a time-offset manner in order to assist a second relative movement between the first and second parts; and
a motor operable to supply energy to or remove energy from the at least one spring to control an amount of energy available from the at least one spring to assist the second relative movement, wherein pivoting the upper part relative to the lower part tensions the spring, moves the adjustable thrust rod, and contacts the limit stop with the adjustable thrust rod.

19. The semi-active orthopedic joint device as claimed in claim 18, wherein the at least one spring includes at least two springs.

20. The semi-active orthopedic joint device as claimed in claim 18, further comprising a damper device arranged between the upper part and the lower part.

21. The semi-active orthopedic joint device as claimed in claim 18, wherein the conversion device re-supplies energy from the at least one spring after initiation of the second relative movement.

* * * * *